United States Patent
Wolff et al.

(10) Patent No.: US 12,014,818 B2
(45) Date of Patent: Jun. 18, 2024

(54) METHOD FOR SETTING AN OPERATIONAL PARAMETER IN A MEDICAL DEVICE

(71) Applicant: Fresenius Vial SAS, Brézins (FR)

(72) Inventors: Rémy Wolff, Tullins (FR); Benjamin Mazas, Le Pecq (FR)

(73) Assignee: Fresenius Vial SAS, Brézins (FR)

( * ) Notice: Subject to any disclaimer, the term of this patent is extended or adjusted under 35 U.S.C. 154(b) by 185 days.

(21) Appl. No.: 17/599,860

(22) PCT Filed: Dec. 13, 2019

(86) PCT No.: PCT/EP2019/085161
§ 371 (c)(1),
(2) Date: Sep. 29, 2021

(87) PCT Pub. No.: WO2020/233827
PCT Pub. Date: Nov. 26, 2020

(65) Prior Publication Data
US 2022/0160963 A1    May 26, 2022

(30) Foreign Application Priority Data
May 17, 2019   (EP) .................................. 19305632

(51) Int. Cl.
*G16H 40/40*   (2018.01)
*G06F 3/0362*   (2013.01)
(Continued)

(52) U.S. Cl.
CPC ............ *G16H 40/40* (2018.01); *G06F 3/0362* (2013.01); *G06F 3/04847* (2013.01); *A61M 2205/502* (2013.01); *G16H 20/17* (2018.01)

(58) Field of Classification Search
None
See application file for complete search history.

(56) References Cited

U.S. PATENT DOCUMENTS

| | | | | |
|---|---|---|---|---|
| 2007/0109325 A1* | 5/2007 | Eveleigh | ............. | G06F 3/04847 345/684 |
| 2008/0184167 A1* | 7/2008 | Berrill | ................. | G06F 3/04847 715/833 |

(Continued)

FOREIGN PATENT DOCUMENTS

| | | | |
|---|---|---|---|
| CN | 106529141 A | * | 3/2017 |
| CN | 106529141 A | | 3/2017 |
| EP | 1952225 A2 | | 8/2008 |

OTHER PUBLICATIONS

International Search Report and Written Opinion, counterpart International Appl. No. PCT/EP2019/085161 (dated Feb. 12, 2020) (14 pages).

*Primary Examiner* — Mandrita Brahmachari
(74) *Attorney, Agent, or Firm* — Cook Alex Ltd.

(57) ABSTRACT

In a method for setting an operational parameter in a medical device (1) an input device (10) is actuated to set an operational parameter (110) displayed on a display device (11) of the medical device (1), wherein the input device (10) is advanceable in an actuation direction (D1, D2) by movement steps (α) to increase or decrease the operational parameter (110) by a change amount associated with a movement step (α). Herein, when advancing the input device (10), said change amount is adapted from a fine-tuning-state value to a tuning-state value larger than the fine-tuning-state value in case a first condition is met. In this way a method for setting an operational parameter in a medical device is provided which allows for an easy and comfortable adjustment of an operational parameter for programming the medical device, for example in the context of an infusion operation.

17 Claims, 2 Drawing Sheets

(51) Int. Cl.
*G06F 3/04847* (2022.01)
*G16H 20/17* (2018.01)

(56) References Cited

U.S. PATENT DOCUMENTS

| | | | |
|---|---|---|---|
| 2010/0313162 A1* | 12/2010 | Preysman | G01D 7/00 |
| | | | 715/781 |
| 2012/0200504 A1* | 8/2012 | DeAngelo | G06F 9/445 |
| | | | 345/184 |
| 2015/0160845 A1* | 6/2015 | Lahtivuori | G06F 3/0488 |
| | | | 715/835 |
| 2015/0187105 A1* | 7/2015 | Endo | G06F 15/0225 |
| | | | 345/589 |
| 2016/0246935 A1 | 8/2016 | Cerny et al. | |
| 2016/0283187 A1* | 9/2016 | Yamamoto | H04H 60/04 |
| 2017/0070659 A1* | 3/2017 | Kievsky | H04N 23/632 |
| 2018/0188284 A1* | 7/2018 | Douglas | G06V 40/23 |

\* cited by examiner

METHOD FOR SETTING AN OPERATIONAL PARAMETER IN A MEDICAL DEVICE

The present application is a U.S. National Stage of PCT International Patent Application No. PCT/EP2019/085161, filed Dec. 13, 2019, which claims priority to EP Application No. 19305632.2, filed May 17, 2019, both of which are hereby incorporated herein by reference.

DESCRIPTION

The invention relates to a method for setting an operational parameter in a medical device according to the preamble of claim 1 and to a medical device.

Within such a method, an input device is actuated to set an operational parameter displayed on a display device of the medical device, wherein the input device is advanceable in an actuation direction by movement steps to increase or decrease the operational parameter by a change amount associated with a movement step.

Within medical devices, for example infusion devices for administering medical fluids to a patient, operational parameters such as a flow rate, a dosage, or a dose rate, need to be programmed for setting up an infusion operation. For such programming, typically, a medical device such as an infusion device comprises an input device for example in the shape of a rotary knob which can be rotated and hence advanced in a stepwise fashion in order to increase or decrease the operational parameter displayed on a display device for programming. By advancing the input device, in this way, the operational parameter is adjusted, each movement step of the input device relating to a change of the operational parameter by a certain change amount such that the operational parameter can be programmed to a desired value.

A range of possible values for an operational parameter may be large and may range for example from 0 to 1 million, due also to the fact that different units may be employed when programming an operational parameter such as the flow rate. Such large range of possible values poses a challenge for the handling of an input device, as the input device shall allow for a comfortable, fast setting of an operational parameter, while reducing the risk for errors in the programming of an operational parameter as much as possible.

It is an object to provide for a method for setting an operational parameter in a medical device and for a medical device which allow for an easy and comfortable adjustment of an operational parameter for programming the medical device, for example in the context of an infusion operation.

This object is achieved by means of a method comprising the features of claim 1.

Herein, the method includes the step of adapting, when advancing the input device, said change amount from a fine-tuning-state value to a tuning-state value larger than the fine-tuning-state value in case a first condition is met.

Within the method an operational parameter for programming a medical device is adjusted by advancing an input device of the medical device. The advancing of the input device herein takes place in a stepwise fashion by advancing the input device step by step, wherein movement steps of the input device cause an adjustment of the operational parameter. Herein, a change amount associated with a movement step is not constant, but depends on the advancing of the input device itself. In particular, the change amount is adapted when advancing the input device from a fine-tuning-state value to a tuning-state value larger than the fine-tuning-state value such that a further advancement of the input device causes a faster change of the operational parameter.

Because the change value associated with a movement step does not remain constant during advancement of the input device, but is adaptively adjusted, a setting of an operational parameter over a large range of possible values is possible at an increased level of comfort and at a higher programming speed. When it is detected that the input device is advanced steadily in a certain actuation direction, it is assumed that a substantial adjustment of the operational parameter is desired, hence causing the change amount to be set from the fine-tuning-state value to the tuning-state value (or an even larger value as described further below) in order to allow for a faster adjustment of the operational parameter.

The adaption of the change amount from the fine-tuning-state value to the tuning-state value takes place if a first condition is met. For examining whether the first condition is met it in particular may be examined whether a frequency at which movement steps occur exceeds a predefined first frequency and/or a number of movement steps exceeds a predefined first number. The frequency of movement steps is indicative of the speed of movement of the input device. If the movement steps occur at a high frequency, this may indicate that a user wishes to substantially change an operational parameter, such that the change amount is set from the fine-tuning-state value to the tuning-state value. In addition, the increase of the change amount to the tuning-state value may take place only if the input device has been advanced over a predefined number of movement steps counted from the beginning of actuation of the input device after the change amount has been set to the fine-tuning-state value (and the input device hence is in the fine-tuning state).

The predefined first frequency may for example lie in a range between 10 Hz and 30 Hz, for example at 15 Hz.

The predefined first number may lie in the range between 15 and 35, for example at 25 movement steps.

If the change amount is set to the fine-tuning-state value or the tuning-state value, the operational parameter may, for example, be changed by the change amount for every movement step by which the input device is advanced. Hence, every movement step of the input device causes a change of the operational parameter by the change amount being currently set to the fine-tuning-state value or the tuning-state value.

In one embodiment, the method may include a step of adapting said change amount from said tuning-state value to a steady-state value larger than the tuning-state value in case a second condition is met. Over a prolonged, continuous movement of the input device the change amount hence is further increased beyond the tuning-state value, such that an even faster adjustment of the operational parameter becomes possible.

For examining whether the second condition is met, it may for example be examined whether a frequency at which the movement steps occur exceeds a predefined second frequency and/or a number of movement steps exceeds a predefined second number. Hence, if the advancement of the input device takes place steadily at a substantial speed, indicated by the frequency of the movement steps, and possibly in addition if after changing the change amount to the tuning-state value an advancement of the input device by a predefined second number of movement step has taken place, the change amount is further increased to the steady-state value, hence allowing for an even faster adjustment of the operational parameter.

The predefined second frequency may for example lie in a range between 10 Hz and 30 Hz, for example at 15 Hz.

The predefined second number of movement steps may lie in between 15 and 35, for example at 25 movement steps after adapting the change amount to the tuning-state value (i.e., after changing from the fine-tuning state to the tuning state).

Whereas every movement step may cause a change of the operational parameter by the change amount when the change amount is set to the fine-tuning-state value (i.e., in the fine-tuning state) or to the tuning-state value (i.e., in the tuning state), the operational parameter is changed, in one embodiment, by the change amount only at every Nth movement step when the change amount is set to the steady-state value (i.e., in the steady state). N herein is larger than 1 such that not every movement step causes an adjustment of the operational parameter by the change amount, but only once N steps have passed the operational parameter is changed by the change amount.

N may for example lie anywhere between 2 and 10, for example at 5.

In one embodiment, the operational parameter is adaptable within a predefined overall range, wherein for adapting said change amount in dependence of the advancing of the input device a first set of values is applied in a first sub-range of the overall range and a second set of values is applied in a second sub-range of the overall range.

The overall range may for example range from 0 to 1 million. The overall range herein may be divided into sub-ranges, for example ranging from 0 to 10,000, from 10,000 to 100,000, and from 100,000 to 1 million. Each sub-range herein may be associated with a particular set of values to which the change amount may be set, i.e., to a particular set of a fine tuning-state value, a tuning-state value and a steady-state value. Once entering a sub-range from another sub-range the now applicable set of values is applied such that for the further advancement of the input device the change amount is adapted according to the now actual set of fine-tuning value, tuning-state value and steady-state value.

In one embodiment, the sub-ranges are consecutive. That is, a first sub-range is bound by a first bound and a second bound, and a second sub-range for example following the first sub-range in the increase direction is bound by the second bound and a third bound larger than the second bound.

When passing from one sub-range to the other, a set of fine tuning-state value, tuning-state value and steady-state value is applied which is associated with the current sub-range. Herein, it may be desirable to cushion a transition from one sub-range into the other by for example pausing a further increase or decrease of the operational parameter for a predetermined amount of time when reaching a bound in between two sub-ranges, for example the second bound in between the first sub-range and the second sub-range. Hence, a user is notified of leaving one sub-range and of entering another sub-range, the increase or decrease of the operational parameter (depending on the actuation direction of the input device) is halted and then continues upon further advancement of the input device.

The predetermined amount of time by which the increase or decrease of the operational parameter is paused when reaching a bound in between two sub-ranges may for example lie in the range between 200 ms and 1000 ms, for example at 500 ms.

Alternatively or in addition, upon reaching a bound in between two sub-ranges when advancing the input device to increase or decrease the operational parameter, the change amount may be set to the fine-tuning-state value associated with the sub-range which now has been entered upon passing the bound in between the sub-ranges. Hence, when entering a sub-range the adjustment of the operational parameter starts anew at the fine-tuning-state value associated with the now current sub-range, wherein the change amount is adapted to the tuning-state value for example if the frequency of the movement steps exceeds a predefined first frequency and if in addition a predefined first number of movement steps have occurred after setting the change amount to the fine-tuning-state value of the sub-range.

The fine-tuning-state value may for example be 1 in a first sub-range, for example between 0 and 10,000. The tuning-state value in the first sub-range may for example be 10, and the steady-state value may be 100.

In a second sub-range following the first sub-range in the increase direction, the values may for example be amplified by 10, such that the fine-tuning-state value becomes 10, the tuning-state value becomes 100, and the steady-state value becomes 1000. The second sub-range may lie for example between 10,000 and 100,000.

In a third sub-range, ranging for example from 100,000 to 1 million, the values may be amplified, with respect to the first sub-range, by 100, such that the fine-tuning-state value becomes 100, the tuning-state value becomes 1000, and the steady-state value becomes 10,000.

In addition, a boost mode may be applied. For example, when the change amount is set to the tuning-state value or the steady-state value, an additional boost of the change amount may be applied, for example by a factor ranging between 2 and 20, for example between 5 and 15, for example 10, once a boost value is passed in a sub-range and the frequency of movement steps exceeds a predefined boost frequency. Each sub-range herein may be associated with its own boost value, the boost value in the first sub-range being for example 1500, the boost value in the second sub-range being 15,000, and the boost value in the third sub-range being 150,000. The predefined boost frequency may for example lie in between 5 Hz and 20 Hz, for example at 10 Hz.

When certain conditions are met, the change amount is increased from the fine-tuning-state value to the tuning-state value, or from the tuning-state value to the steady-state value. In turn, at other conditions the change amount may be decreased from the steady-state value to the tuning-state value, or from the tuning-state value to the fine-tuning-state value, or from the steady-state value directly to the fine-tuning-state value.

For example, if the change amount is set to the steady-state value, if a time duration of a movement step exceeds a predefined steady-state timeout, for example lying between 100 ms and 300 ms, for example at 200 ms, the change amount may be reset to the tuning-state value. If the change amount is set to the tuning-state value, the change amount may be adapted to the fine-tuning-state value in case the time duration of a movement step exceeds a predefined tuning-state timeout, for example lying in between 100 ms and 1000 ms, for example at 500 ms.

Generally, independent from the value to which the change amount currently is set, the change amount may be reset to the fine-tuning-state value if a break condition is met. The break condition may for example include an examination whether a movement step occurs within a predefined break time, and if no movement step occurs within the predefined break time the break condition is met such that the change amount is reset to the fine-tuning-state value. Hence, upon fulfilling the break condition the change amount is set to the lowest value possible in the current sub-range such that a fine adjustment of the operational parameter is possible.

The break time may for example be 1000 ms or larger.

Another break condition may be whether the actuation direction of the input device is reversed, causing the change amount to be reset to a lower state, for example from the steady-state value to the tuning-state value or immediately to the fine-tuning-state value.

In addition, when a break condition is met, for example the counter for counting the movement steps for changing the change amount from the tuning-state value to the steady-state value (i.e., to change from the tuning state to the steady-state) may be cleared, and in addition a memory for computing a frequency of movement steps may be reset.

In one embodiment, the frequency of movement steps is calculated by averaging individual frequencies of single movement steps. Herein, each individual frequency is computed as the inverse of a time duration of a particular single movement step, i.e., based on the time duration between subsequent ticks of for example a rotary knob which is advanceable tick by tick in a stepwise fashion. The frequency of movement steps is hence computed from a running average of the movement of the input device, wherein the average may be taken over a predefined number of movement steps, for example a number in between 10 and 30, for example 20.

When the input device has the shape of a rotary knob, generally a user may rotate the input device by turning his wrist. As it can be assumed that a user may turn his wrist only by a certain angle (for example about 180°) before turning his wrist back to start rotating the input device anew, it may be taken into account for computing the frequency of movement steps that a user may naturally have to interrupt the actuation of the input device repeatedly, such interruption not being indicative of a break in the adjustment of the operational parameter.

Hence, when computing the frequency of movement steps by averaging individual frequencies of single steps, a predefined number of individual frequencies smaller than a predefined frequency limit may be disregarded, assuming that such frequencies may be due to a user moving his wrist to start an actuation of the input device anew. For example, one individual frequency smaller than a predefined frequency limit, for example 10 Hz, may be disregarded when averaging individual frequencies of for example 20 movement steps. If a second and third individual frequency is smaller than set predefined frequency limit, however, such individual frequencies may be taken into account for computing the frequency of movement steps.

In one embodiment, a rounding may be applied. The rounding herein may for example be synchronized to the currently used change amount. That is, if the change amount is for example set to 10, the operational parameter may be changed with the second-to-last digit being the smallest significant digit. Hence, a sequence of the operational parameter may be 870-880-890 and so on when applying the change amount. If the change amount instead is set to 100, the third-to-last digit may be the smallest significant digit when increasing or decreasing the operational parameter, such that a sequence may read 12300-12400-12500 and so on.

Herein, even if a prior value of the operational parameter had a smaller significant digit, for example the last, smallest digit (e.g., 12448), when applying the change amount a rounding may be applied according to the value of the change amount. If the change amount for example is set to 100 and the operational parameter at the outset is 12448, a rounding may be applied to obtain a sequence such as 12500-12600-12700 and so on, hence using a smallest significant digit when applying the change amount according to the actual value of the change amount.

The object is also achieved by a medical device comprising: a display device, an input device which is actuatable to set an operational parameter displayed on the display device of the medical device, wherein the input device is advanceable in an actuation direction by movement steps to increase or decrease the operational parameter by a change amount associated with a movement step, and a control device for controlling operation of the medical device. Herein, the control device is configured to adapt, during advancement of the input device, said change amount from a fine-tuning-state value to a tuning-state value larger than the fine-tuning-state value in case a first condition is met.

The advantages and advantageous embodiments described above for the method equally apply to the medical device, such that it shall be referred to the above in this respect.

The medical device may for example be an infusion device, such as a volumetric (peristaltic) infusion pump or a syringe infusion pump.

The input device may for example have the shape of a rotary knob being rotatable about a rotational axis, each movement step being associated with a predefined step angle. For example, the input device in the shape of the rotary knob may be rotatable by discrete steps, a full turn being comprised for example of a number between 20 and 40 steps, for example 30 steps. In case a full turn is comprised of 30 steps, the step angle associated with one movement step equals 12°.

It shall be noted that the input device may have any conceivable structure and configuration different than a rotary knob. For example, the input device may have the shape of a touchpad allowing an advancement by movement steps for adjusting an operational parameter in discrete steps for example by sliding over the touchpad.

In principle, any input device allowing for an endless actuation may be conceivable and applicable for carrying out an input operation as described herein.

Figure 1:
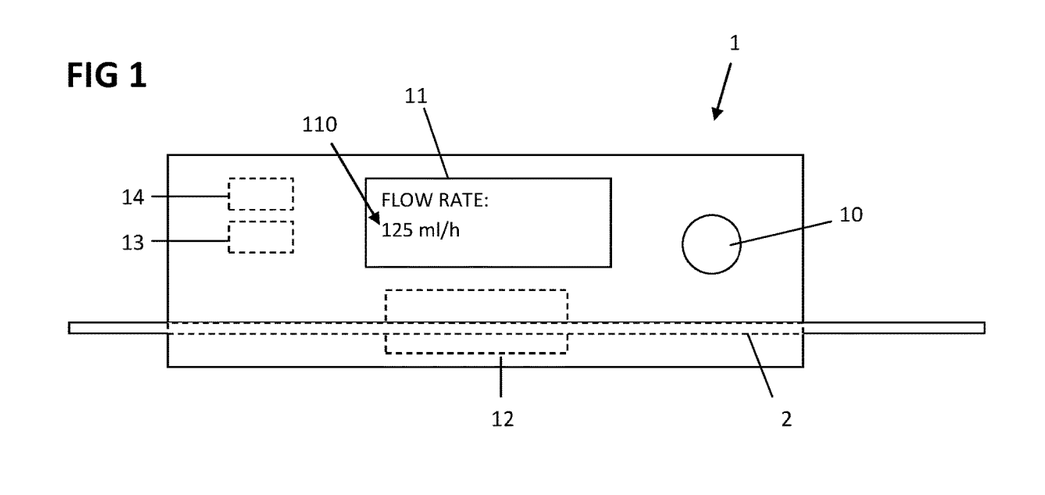
FIG. 1 shows a schematic drawing of a medical device in the shape of an infusion device.

The invention shall subsequently be described in more detail according to the embodiments shown in the figures. Herein:

FIG. 1 shows a schematic drawing of a medical device 1 in the shape of an infusion device which serves to administer a medical fluid to a patient.

The medical device 1 in the shape of the infusion device herein comprises a receptacle on which an infusion set 2 may be received, the infusion set 2 comprising an infusion line through which a medical fluid may be delivered towards the patient. When received on the medical device 1, the infusion set 2 is functionally connected to a pumping mechanism 12 of the medical device 1, the pumping mechanism 12 causing a delivery of a medical fluid through the infusion set 2 when the pumping mechanism 12 is operated.

The medical device 1 comprises a control device 13 and a memory device 14, which together are configured to control operation of the medical device 1, in particular for performing an infusion operation for administering a medical fluid towards a patient.

Figure 2:
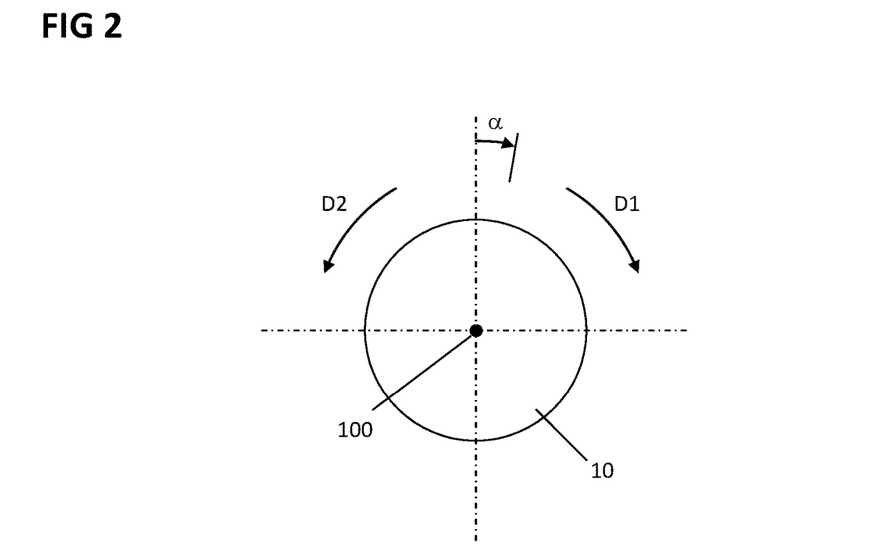
FIG. 2 shows a schematic drawing of an input device in the shape of a rotary knob.

The medical device 1 comprises an input device 10 in the shape of a rotary knob which, as illustrated in the schematic drawing of FIG. 2, is rotatable about a rotational axis 100 and can be activated for setting an operational parameter 110 for programming the operation of the medical device 1, in particular for programming and setting up in infusion operation.

The medical device 1 furthermore comprises a display device 11 for displaying information, for example for displaying actual values of operational parameters 110 such as the flow rate, a dosage or the dose rate. The display device 11 furthermore may output information about an ongoing operation of the medical device 1, for example in the context of an infusion operation, such as information relating to a progress of an infusion operation.

Generally, for setting up an infusion operation, an operational parameter 110 such as a flow rate may be set by actuating the input device 10. Herein, an operational parameter 110 to be set may be selected via a menu displayed on the display device 11, wherein a particular operational parameter 110 may be adjusted upon selection by actuating the input device 10 to program the medical device 1 for carrying out an infusion operation.

Herein, as indicated in FIG. 2, the input device 10 may be rotated about the rotational axis 100 in a first, clockwise actuation direction D1 for increasing a selected operational parameter 110, and in a second, counterclockwise actuation direction D2 for decreasing the selected operational parameter 110. Hence, by rotating the input device 10 in the shape of the rotary knob an increase as well as a decrease of the operational parameter 110 is possible for setting the operational parameter 110, for example the flow rate, to a particular, desired value.

The rotary knob making up the input device 10, in one embodiment, is actuatable in an endless fashion such that the input device 10 may be rotated about the rotational axis 100 in either direction D1, D2 without any bound. The input device 10 herein may be rotatable by discrete movement steps, each movement step relating to a particular step angle α, as illustrated in FIG. 2. The movement steps herein may be discrete in that the movement steps are defined by mechanical notches, the input device 10 being discreetly movable in between defined detent positions separated by the step angle α, such that the input device 10 is moved step by step, but may not assume an immediate position in between two discrete steps.

Generally, a rotation of the input device 10 about the rotational axis 100 causes an adjustment of the currently selected operational parameter 110 in dependence of the movement direction of the input device 10. Each movement step herein has an influence on an increase or decrease of the operational parameter 110, dependent on whether the input device 10 is moved in the first actuation direction D1 or in the second actuation direction D2.

Generally, a movement step by which the input device 10 is moved is associated with a change amount by which the operational parameter 110 is changed when advancing the input device 10 in one direction D1, D2 or the other. Herein, it is proposed to adapt the change amount such that a change of the operational parameter 110 when advancing the input device 10 in one direction D1, D2 or the other depends on the movement of the input device 10 itself.

In this way, an adjustment of the operational parameter 110 over a wide range, for example in between 0 and 1 million, becomes possible in a fast, comfortable manner, which may be necessary due to the fact that an operational parameter 110 may be set according to different units and hence may assume values within a fairly wide range.

Figure 3:
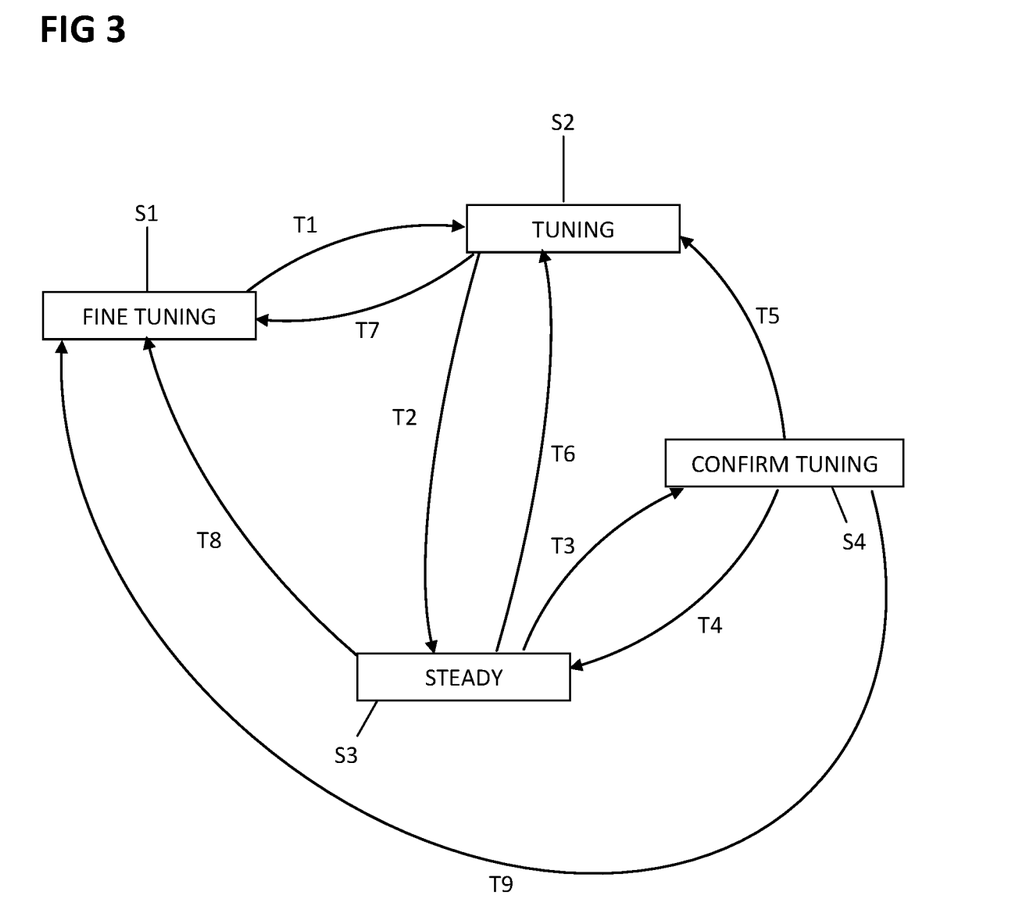
FIG. 3 shows a state diagram of different states of the input device for adjusting an operational parameter for programming a medical device.

Referring now to FIG. 3, the input device 10, controlled by the control device 13 together with the memory device 14, may be operated by employing different control states S1, S2, S3, S4, each state being associated with a particular change amount in order to cause an increase or decrease of the currently selected operational parameter 110.

Generally, an adjustment of the operational parameter 110 starts in a fine-tuning state S1, in which a change amount is set to a fine-tuning-state value corresponding for example to a smallest applicable change unit. Assuming that the operational parameter 110 shall be changed by integers, the fine-tuning-state value may for example be set to 1. Hence, in the fine-tuning state S1 a movement of the input device 10 causes a change of the operational parameter 110 by the fine-tuning-state value, such that each movement step of the input device 10 causes an increase or decrease of the operational parameter 110 by the fine-tuning-state value.

In case a first condition is met, the operation of the input device 10 may change from the fine-tuning state S1 to a tuning state S2 (transition T1). In particular, if a frequency of movement steps exceeds a predefined first frequency, and if in addition the input device 10 has been advanced over a predefined first number of movement steps while in the fine-tuning state S1, the operation may transition from the fine-tuning state S1 to the tuning state S2, the tuning state S2 being associated with a tuning-state value larger than the fine-tuning-state value. Hence, the change amount now is set to the tuning-state value, such that a further advancement of the input device 10 causes a faster change of the operational parameter 110.

The first frequency may for example lie in between 10 Hz and 30 Hz, for example at 15 Hz. The first number of movement steps may for example lie in between 15 and 35, for example at 25.

If the fine-tuning-state value is 1, the tuning-state value may for example be 10. Hence, for each movement step of the input device 10 the operational parameter 110 in the tuning state is changed by 10, such that the speed of change of the operational parameter 110 is amplified by a factor of 10.

When in the tuning state S2, operation may further transition to a steady state S3 (transition T2) in case a second condition is met. In particular, if the frequency of movement steps exceeds a second frequency, and if the input device 10 has been advanced over a predefined second number of movement steps while in the tuning state S2, the control may transition from the tuning state S2 to the steady state S3. The steady state S3 is associated with a steady-state value, such that in the steady state S3 the change amount is set to the steady-state value associated with the steady state S3. Hence, a further advancement of the input device 10 in the steady state S3 causes a change of the operational parameter 110 by the steady-state value.

If the fine-tuning-state value is 1 and the tuning-state value is 10, the steady-state value may for example be 100.

Whereas in the fine-tuning state S1 and in the tuning state S2 each movement step may cause a change of the operational parameter 110 by the change amount (i.e., the fine-tuning-state value in the fine-tuning state S1 or the tuning-state value in the tuning state S2), in the steady state S3 the operational parameter 110 is, in one embodiment, adjusted by the steady-state value only after every Nth movement step, wherein N may for example lie between 2 and 10, for example at 5. Hence, only after the input device 10 has been advanced over N movement steps in the steady state S3, the operational parameter 110 is adjusted by the steady-state value, for example 100.

The overall range over which the operational parameter 110 may be adjustable may for example be bound by 0 and 1 million. Hence, by actuating the input device 10 the operational parameter 110 may be changed in between 0 and 1 million. The overall range herein may be divided into sub-ranges, a first sub-range for example ranging from 0 to 10,000, a second sub-range ranging from 10,000 to 100,000, and a third sub-range ranging from 100,000 to 1 million. Each sub-range herein may be associated with its particular set of fine-tuning-state value, tuning-state value and steady-state value, wherein the values may be amplified by an amplification factor of 10 from one sub-range to the other in order to allow for a faster adjustment of the operational parameter 110 over the sub-ranges.

For example, in the first sub-range ranging from 0 to 10,000, the fine-tuning-state value may be 1, the tuning-state value may be 10 and the steady-state value may be 100.

In the second sub-range ranging from 10,000 to 100,000, the fine-tuning-state value may be 10, the tuning-state value may be 100, and the steady-state value may be 1000.

In the third sub-range ranging from 100,000 to 1 million, the fine-tuning-state value may be 100, the tuning-state value may be 1000, and the steady-state value may be 10,000.

When starting an adjustment of the operational parameter 110 at 0, the adjustment of the operational parameter 110 first takes place by applying the fine-tuning-state value having the value 1. If a certain number of movement steps, for example 25, has been exceeded and if the speed of movement of the input device 10, as indicated by the frequency of the movement steps, exceeds a predefined first frequency, for example 15 Hz, it is changed to the tuning state S2, and the change amount applied to the operational parameter 110 per movement step is set to the tuning-state value having a value of 10. If in the tuning state S2 the input device 10 is further advanced by a predefined second number of movement steps, for example 25, and if the frequency of movement steps exceeds a second frequency, for example 15 Hz, it is transitioned to the steady state S3, and the change amount is set to the steady-state value having a value of 100, wherein the steady-state value is applied only at every Nth movement step, for example at every fifth movement step.

If a certain boost value, for example 1500, is reached in the first sub-range, a further boost factor of 10 may be applied, boosting the change amount by the factor of 10 such that a further advancement of the input device 10 beyond the boost value causes in amplified, boosted increase of the operational parameter 110.

If the upper bound of the first sub-range at 10,000 is reached, it is transitioned into the consecutive, second sub-range ranging from 10,000 to 100,000. At the bound, the increase of the operational parameter 110, in one embodiment, is paused for a predefined pause time, for example 500 ms. Hence, the transition from one sub-range to another is cushioned by the pause time.

In addition, upon entrance of a new sub-range the change amount is set to the fine-tuning-state value of the entered sub-range, such that the acceleration of the adjustment of the operational value 110 starts anew at the fine-tuning-state value of the now current sub-range.

The operation now progresses as in the first sub-range, wherein upon passing a particular boost value associated with the second sub-range, for example 15,000, a boost of the change amount by a boost factor of for example 10 may be applied.

At the transition from the second sub-range to the third sub-range ranging from 100,000 to 1 million, again a pause by a predefined pause time may be applied, and the acceleration starts anew at the fine-tuning-state value associated with the now current, third sub-range. An additional boost may be applied after passing a boost value of 150,000.

If it is detected that the time duration of a movement step, for example in the steady state S3, exceeds a predefined steady-state-timeout, for example 200 ms, operation may transition from the steady state S3 to a confirm-tuning state S4 (transition T3 in FIG. 3). In the confirm-tuning state S4 it may be decided whether to transition to the tuning state S2 (transition T5) or to transition back to the steady state S3 (transition T4), dependent on whether the next movement step takes place within a rather short time duration or exceeds a predefined timeout.

If in the confirm-tuning state S4 no movement step occurs within a time duration defined by a tuning-state-timeout, operation shall pass to the fine-tuning state S1 (transition T9). If instead the next movement step occurs faster than the tuning-state-timeout, but at a time duration exceeding a confirm-tuning-timeout, it is transitioned from the confirm-tuning state S4 to the tuning state S2 (transition T5). If instead the next movement step occurs faster than the confirm-tuning-timeout, it is transitioned back to the steady state S3 (transition T4).

The steady-state-timeout may for example have a value of 200 ms.

The tuning-state-timeout may for example have a value of 500 ms.

The confirm-tuning-timeout may for example have a value of 100 ms.

In any state S2, S3, S4 other than the fine-tuning state S1, if the time duration for a next movement step exceeds a predefined break time, for example 1000 ms, it is directly switched to the fine-tuning state S1 (transitions T7, T8, T9).

In addition, it is transitioned directly to the tuning state S2 (transition T6) if in the steady state S3 a reversal in the movement of the input device 10 is detected.

In the tuning state S2, a reversal of the movement direction of the input device 10 causes a transition from the tuning state S2 to the fine-tuning state S1 (transition T7).

The boost mode may remain activated (such that a boost factor of for example 10 is applied) as long as it is not switched back to the fine-tuning state S1.

Generally, the same concept may be applied in the increase direction (actuation direction D1 of the input device 10 as illustrated in FIG. 2) and in the decrease direction (corresponding to the actuation direction D2 of the input device 10).

Herein, in the decrease direction, prior to reaching 0, at the decade change at 1000 the actual, current change amount may be divided by a factor of 10 in order to avoid that the operational parameter 110 is changed abruptly to 0 (in a sequence 2000-1000-0 when in the boost mode), such that below 1000 a change amount divided by a factor of 10 is applied, leading to a sequence 2000-1000-900 and so on.

Throughout the increase or decrease of the operational parameter 110, a rounding may be applied, such that always only for relevant digits are changed, whereas the others are rounded.

The frequency of the movement steps is indicative of the movement speed of the input device 10 and may be computed as a running average over a certain number of individual movement steps. Individual frequencies of the individual movement steps herein are computed as the inverse of the time duration of the particular movement step. An average may be taken for example over 20 movement steps.

Herein, for the computation of the frequency by averaging over the individual frequencies for example one individual frequency below 10 Hz may be disregarded. If the input device 10 is rotatable by discrete steps of 12° such that 30 steps make up on full turn, it can be assumed that a user may have to interrupt a rotational movement roundabout at a half turn due to the user having to return his wrist to continue actuation. This causes a break in the movement, which however is not indicative of a desired break in the actuation. Hence, one delayed movement step in a sequence of movement steps is assumed to be due to a returning movement of a user's wrist and therefore is neglected in the averaging for computing the averaged frequency of the movement steps in the above described scheme of controlling acceleration of an adjustment of the operational value 110.

The idea underlying the invention is not limited to the embodiments described above, but may be implemented in an entirely different fashion.

In particular, the input device is not limited to a rotary knob, but may be implemented by a different device, in particular any device that allows for an endless actuation, such as a touchpad device or the like.

A scheme as described herein is suitable to adjust an operational parameter in a medical device, wherein all kinds of different operational parameters may be adjusted by actuation of an input device as described herein. In principle, a scheme as described herein may be applicable to any device that requires an adjustment of an operational parameter over a fairly wide range.

LIST OF REFERENCE NUMERALS

1 Medical device
10 Input device
100 Rotational axis
11 Display device
110 Operational parameter
12 Pumping mechanism
13 Control device
14 Memory device
2 Infusion set
α Movement step (tick angle)
D1, D2 Actuation direction
T1-T9 Transition
S1-S4 State

The invention claimed is:

1. A method for setting an operational parameter in a medical device, comprising:
 actuating an input device to set an operational parameter displayed on a display device of the medical device,
 wherein the input device is advanceable in an actuation direction by movement steps to increase or decrease the operational parameter by a change amount associated with one of the movement steps and wherein the operational parameter is adjustable over a predefined overall numeric range with at least a first predefined numeric sub-range within the predefined overall numeric range and a second predefined numeric sub-range within the predefined overall numeric range,
 wherein each sub-range is associated with different predefined change amounts for a fine-tuning-state numeric value and a tuning-state numeric value by which the operational parameter is adjusted when in the respective state, and
 adapting, when advancing the input device within a subrange, said change amount from the fine-tuning-state numeric value to the tuning-state numeric value larger than the fine-tuning-state numeric value in case a first condition is met,
 wherein adapting said change amount in dependence of the advancing of the input device comprises applying a first set of values with the operational parameter in the first predefined numeric sub-range of the predefined overall numeric range and applying a second set of values with the operational parameter in the second predefined numeric sub-range of the predefined overall numeric range.

2. The method according to claim 1, further comprising examining whether the first condition is met, said examining comprising whether a frequency at which movement steps occur exceeds a predefined first frequency and/or a number of movement steps exceeds a predefined first number.

3. The method according to claim 1, wherein when the change amount is set to the fine-tuning-state numeric value or the tuning-state numeric value, the operational parameter is changed by the change amount for every movement step by which the input device is advanced.

4. The method according to claim 1, further comprising adapting said change amount from said tuning-state numeric value to a third numeric value larger than the tuning-state numeric value in case a second condition is met.

5. The method according to claim 4, further comprising examining whether the second condition is met, said examining comprising whether a frequency at which the movement steps occur exceeds a predefined second frequency and/or a number of movement steps exceeds a predefined second number.

6. The method according to claim 4, wherein when the change amount is set to the third numeric value, the operational parameter is changed by the change amount at every Nth movement step when advancing the input device, wherein N is larger than 1.

7. The method according to claim 1, wherein the first predefined numeric sub-range is bound by a first bound and a second bound and the second predefined numeric sub-range is bound by said second bound and a third bound.

8. The method according to claim 7, wherein upon reaching said second bound when advancing the input device to increase or decrease the operational parameter, the increase or decrease of the operational parameter is paused for a predetermined amount of time.

9. The method according to claim 7, wherein upon reaching said second bound when advancing the input device to increase or decrease the operational parameter, the change amount is set to the fine-tuning-state numeric value associated with the predefined numeric sub-range which is entered upon passing the second bound.

10. The method according to claim 1, further comprising resetting the change amount to the fine-tuning-state numeric value if a break condition is met.

11. The method according to claim 10, further comprising examining whether the break condition is met, said examining comprising whether no movement step occurs for a pre-defined break time.

12. The method according to claim 1, further comprising calculating a frequency of movement steps by averaging individual frequencies of single movement steps, each individual frequency being computed as the inverse of a time duration of a particular single movement step.

13. The method according to claim 12, wherein a predefined number of individual frequencies smaller than a predefined frequency limit is not taken into account for calculating the frequency of movement steps.

14. A medical device, comprising:

a display device, an input device which is actuatable to set an operational parameter displayed on the display device of the medical device, wherein the input device is advanceable in an actuation direction by movement steps to increase or decrease the operational parameter by a change amount associated with one of the movement steps and wherein the operational parameter is adjustable over a predefined overall numeric range with at least a first predefined numeric sub-range within the predefined overall numeric range and a second predefined numeric sub-range within the predefined overall numeric range, wherein each sub-range is associated with different predefined change amounts for a fine-tuning-state numeric value and a tuning-state numeric value by which the operational parameter is adjusted when in the respective state, and a control device for controlling operation of the medical device, the control device being configured to adapt, during advancement of the input device within a sub-range, said change amount from the fine-tuning-state numeric value to the tuning-state numeric value larger than the fine-tuning-state numeric value in case a first condition is met, wherein the control device is configured to adapt said change amount in dependence of the advancement of the input device by being configured to apply a first set of values with the operational parameter in the first predefined numeric sub-range of the predefined overall numeric range and to apply a second set of values with the operational parameter in the second predefined numeric sub-range of the predefined overall numeric range.

15. The medical device according to claim 14, wherein the first predefined numeric sub-range is bound by a first bound and a second bound and the second predefined numeric sub-range is bound by said second bound and a third bound.

16. The medical device according to claim 15, wherein upon reaching said second bound when advancing the input device to increase or decrease the operational parameter, the control device is configured to pause the increase or decrease of the operational parameter for a predetermined amount of time.

17. The medical device according to claim 15, wherein upon reaching said second bound when advancing the input device to increase or decrease the operational parameter, the control device is configured to set the change amount to the fine-tuning-state numeric value associated with the predefined numeric sub-range which is entered upon passing the second bound.

* * * * *